US00PP21199P3

(12) United States Plant Patent
Takeuchi

(10) Patent No.: US PP21,199 P3
(45) Date of Patent: Aug. 17, 2010

(54) ROSE PLANT NAMED 'KEISHISUTOKI'

(50) Latin Name: *Rosa hybrida*
Varietal Denomination: Keishisutoki

(75) Inventor: Shunsuke Takeuchi, Chiba-Ken (JP)

(73) Assignee: Keisei Rose Nurseries, Inc. (JP)

( * ) Notice: Subject to any disclaimer, the term of this patent is extended or adjusted under 35 U.S.C. 154(b) by 0 days.

(21) Appl. No.: 12/231,515

(22) Filed: Sep. 2, 2008

(65) Prior Publication Data

US 2009/0089902 P1 Apr. 2, 2009

(51) Int. Cl.
*A01H 5/00* (2006.01)

(52) U.S. Cl. ..... Plt./104; Plt./145

(58) Field of Classification Search ..... Plt./101, Plt./104, 134, 135
See application file for complete search history.

*Primary Examiner*—Annette H Para
*Assistant Examiner*—Louanne C Krawczewicz Myers
(74) *Attorney, Agent, or Firm*—Klarquist Sparkman, LLP

(57) ABSTRACT

*Rosa* L. rose plant that is bushy, disease resistant, with medium size, flat-shaped yellow flowers.

6 Drawing Sheets

Genus and species: *Rosa hybrida.*
Variety denomination: 'Keishisutoki'.

Origin of the Invention

The present invention relates to a new and distinct variety of a *Rosa* L. rose plant named 'Keishisutoki' which was originated by me by crossing the variety 'MEILOMIT' seed parent (unpatented), with the variety 'Evergold' pollen parent (unpatented).

BACKGROUND OF THE INVENTION

The primary objective of this breeding was to produce a new rose variety that is strong, disease resistant, and vigorous, having yellow, single or semi-double big-middle size flowers suitable for Japanese and western style gardens.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. The new variety is bushy;
2. The new variety has yellow flowers;
3. The new variety has a flat flower shape;
4. The new variety is vigorous and disease resistant.

Asexual reproduction of this new variety by cuttings/budding, as performed at Sawara city in Chiba-ken, Japan, shows that the foregoing and all other characteristics and distinctions come true to form and are established and transmitted through succeeding propagations.

Comparison with Parents

Compared to its mother, the new variey has different color, yellow for the new variety, pale-yellowish pink for 'MEILOMIT'; the new variety is bushy in comparison to 'MEILOMIT', which is half climbing; and flower shape is flat for the new variety in comparison to cup-shaped for 'MEILOMIT'. Compared to its father 'Evergold', the flowers of the new variety have a more intensive yellow color and more petals than 'Evergold'; and the new variety is bushy in comparison to 'Evergold', which is climbing.

Comparison with Similar Variety

Compared to 'AMANOKAWA' (unpatented), the plant grows four times higher and is more vigorous.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
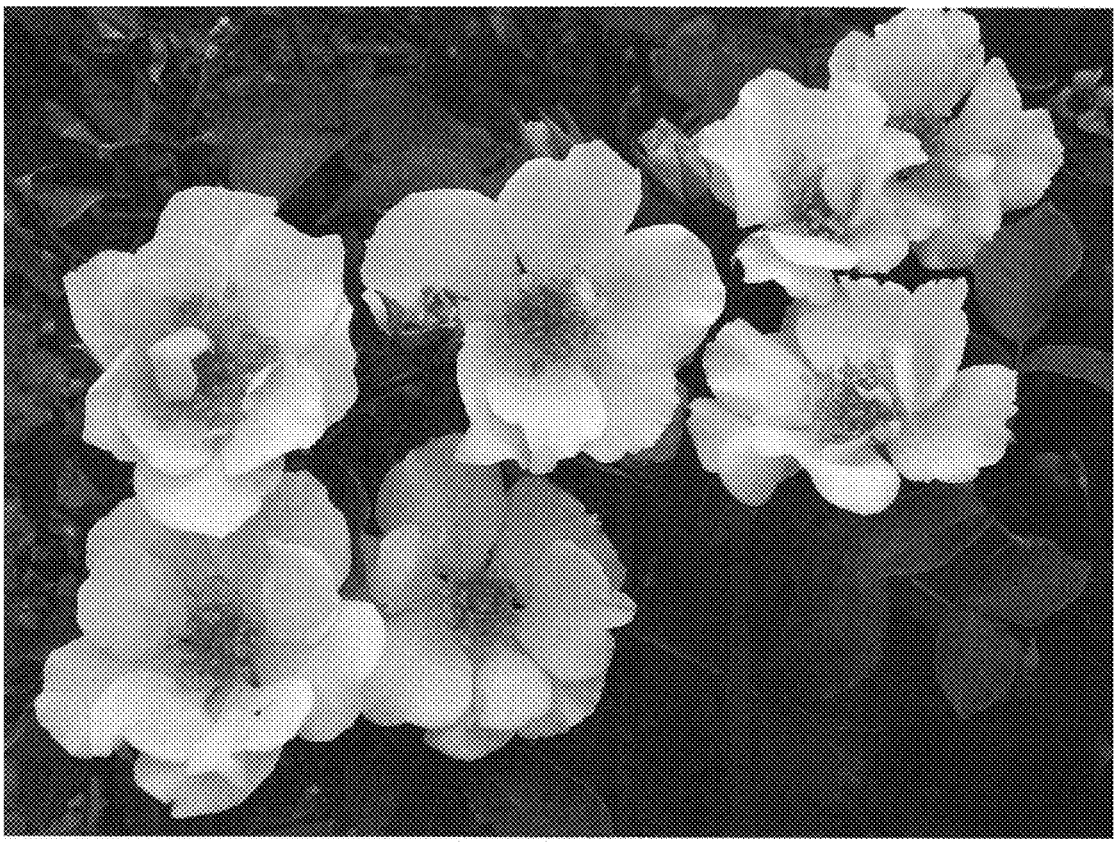
FIG. 1 is a photograph of a group of flowers of the new variety.
Figure 2:
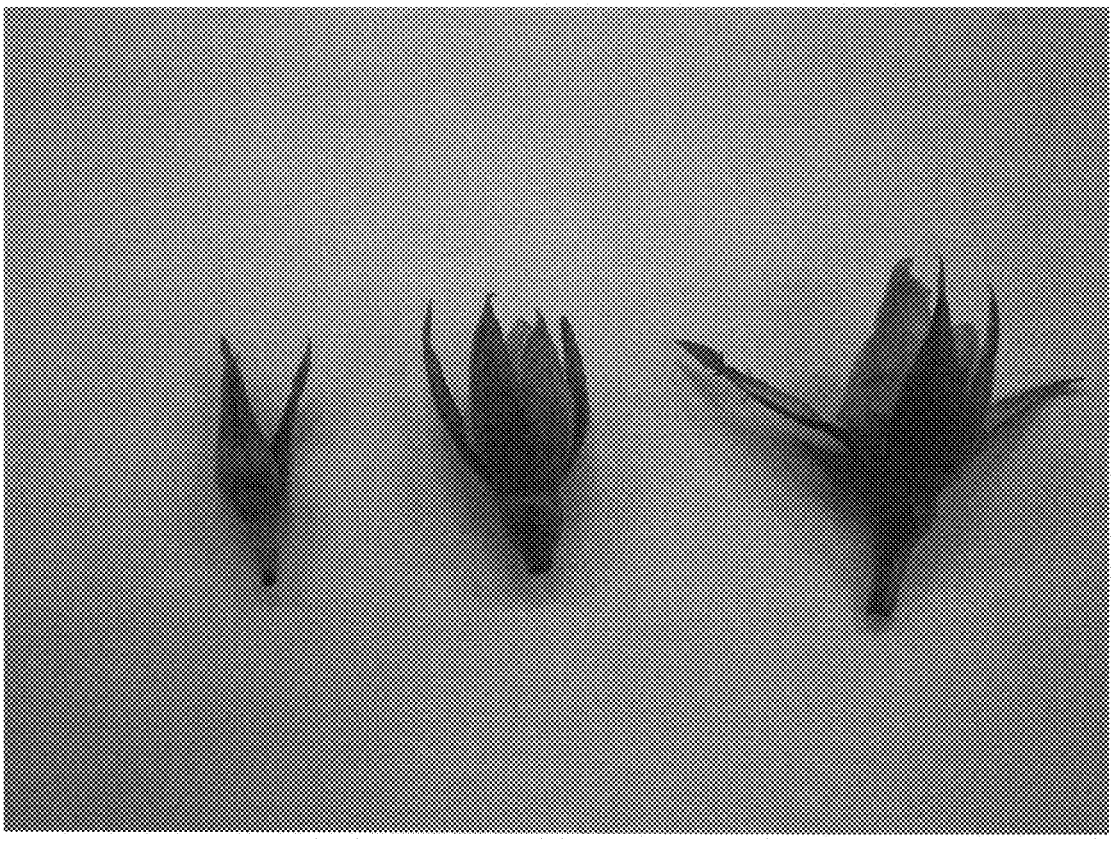
FIG. 2 is a photograph of buds of the new variety in stages of opening.
Figure 3:
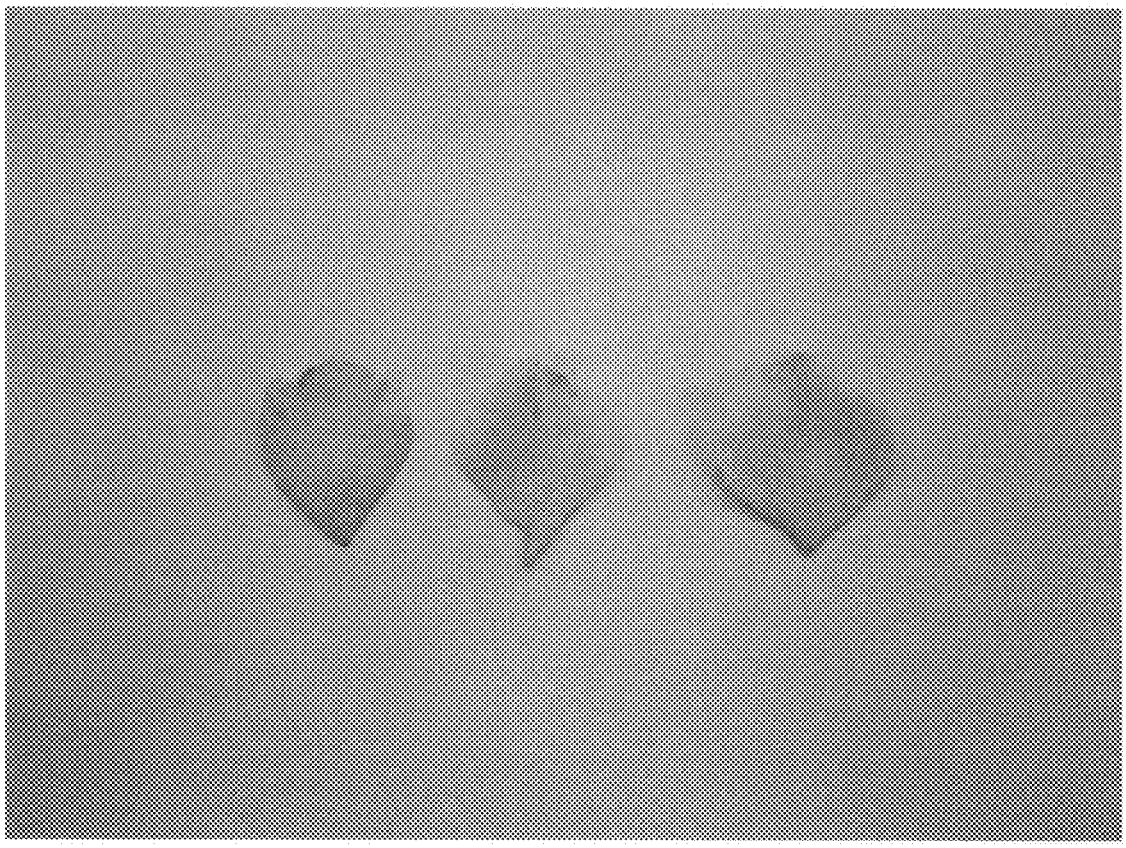
FIG. 3 is a photograph of several flower petals of the new variety.
Figure 4:
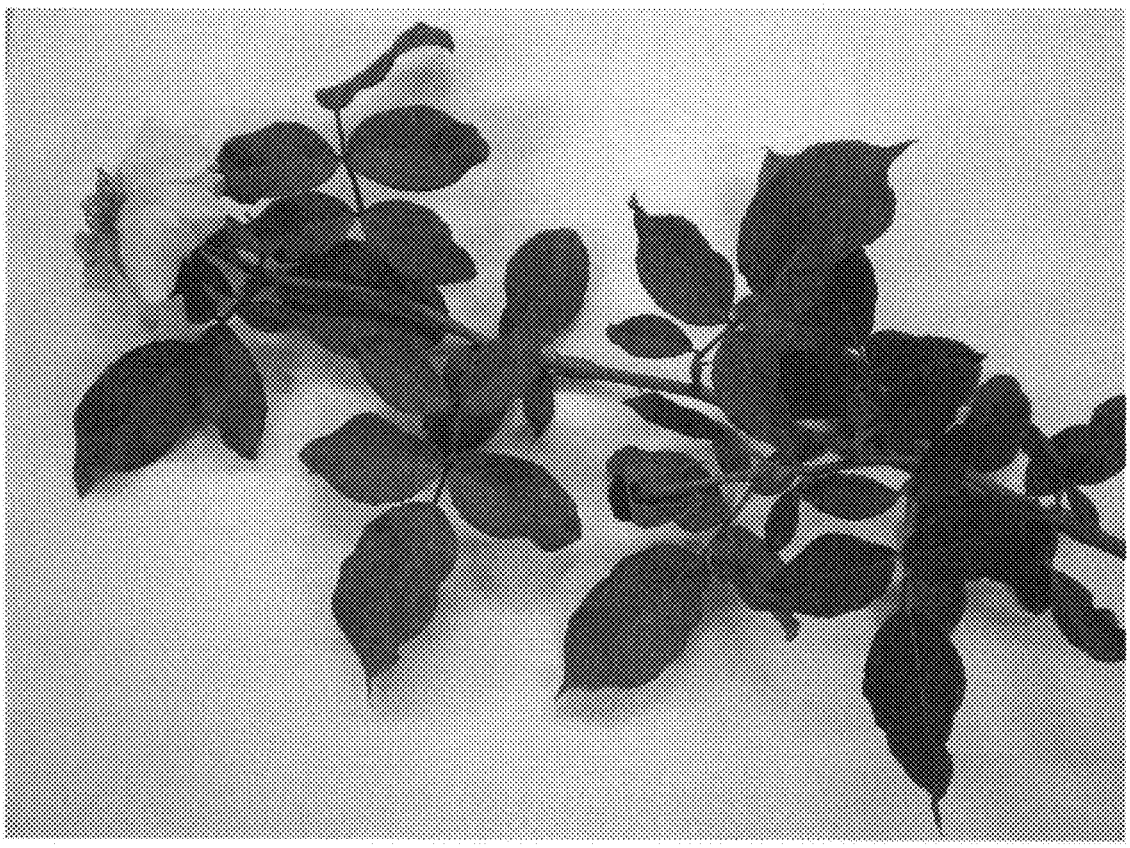
FIG. 4 is a photograph showing the upper surface of foliage of the new variety.
Figure 5:
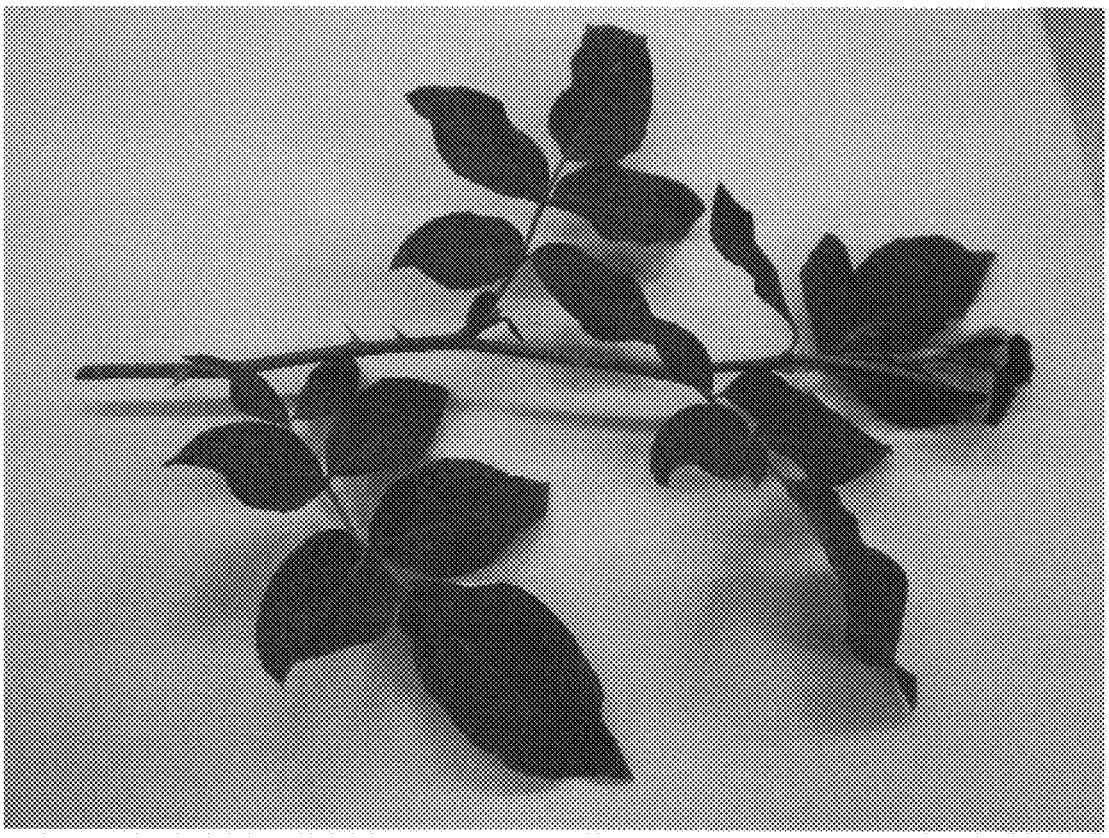
FIG. 5 is a photograph showing the lower surface of foliage of the new variety.
Figure 6:
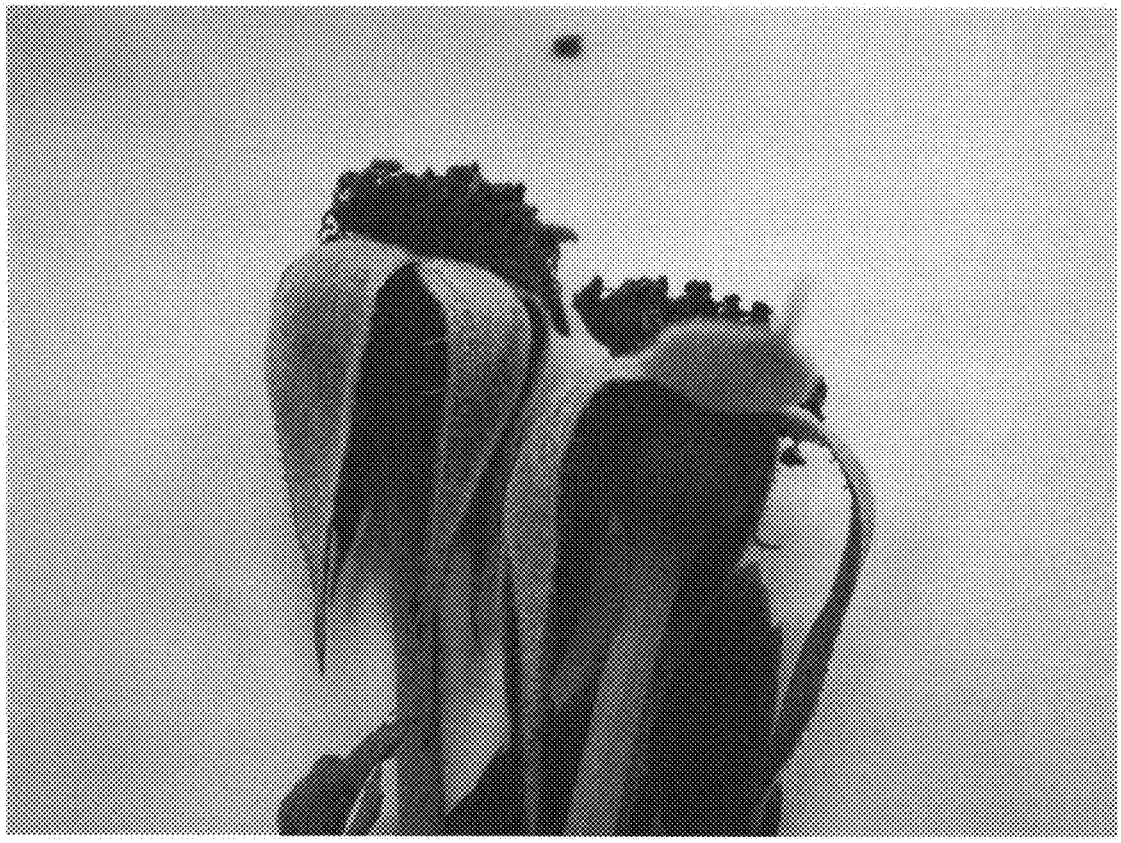
FIG. 6 is a close up of photograph of plant receptacles and sepals of the new variety.

The following is a detailed description of my new rose cultivar with color descriptions using terminology in accordance with the Japan Horticultural Society Color Chart (1984), except where ordinary dictionary significance of color is indicated.

Parentage:

Seed parent.—'MEILOMIT' (unpatented).

Pollen parent.—'Evergold' (unpatented).

FLOWER

Observations made from plants that were about three years of age grown in a garden environment at Sawara-shi, Chiba-ken, Japan.

Blooming habit: Continuous.

Bud:

*Size.*—About 1.2 inches long and 0.4 inches in diameter when the petals start to unfurl.

*Form.*—The bud form is pointed ovoid.

*Color.*—When sepals first divide, bud color is JHS 1905 (bright yellowish orange). When half blown, the upper sides of the petals are JHS 1604 (bright orange); and the lower sides of the petals are JHS 1905 (bright yellowish orange).

*Sepals.*—Color: Upper surface: JHS 3513 (dull yellow green). Lower surface: JHS 3307 (deep yellow green). Length: about 1 inch. Width: about 0.3 inch. Shape: Sepal apex — acute; sepal base — round. Surface texture: Rough on both the upper and lower surfaces. There are three lightly appendaged sepals with serrated edges. Number of sepals: five.

*Receptacle.*—Color: JHS 3311 (strong yellow green). Shape: Pear. Size: Small, about 0.3 inch long×about 0.3 inch wide. Surface: Smooth.

*Peduncle.*—Length: Short, averaging about 1.2 inches. Diameter: Typical and observed about 0.1 inch. Surface: Rough. Color: JHS 3311 (strong yellow green). Strength: Erect.

Bloom:

*Type.*—Floribunda (in rose classification).

*Size.*—Medium. Average open diameter is about 2.8 inches to about 3.2 inches. Typical height of flower about 0.8 inch to about 1.2 inches.

*Borne.*—Several together. Number of flowers per lateral stem is typically 5. Abundant flower habit. One observed plant at one observation had thirty flowers.

*Stems.*—Strength: Weak. Average length is about 10 inches with a diameter of 0.2 inches.

*Form.*—When first open: Flat. Permanence: Retains its form to the end.

*Petalage.*—Number of petals under normal conditions: 10-15.

*Color.*—The upper sides of the petals are JHS 2504 (light yellow). The reverse sides of the petals are JHS 2504 (light yellow). The base of each petal has JHS 2505 (bright yellow). The major color on the upper side is JHS 2504 (light yellow).

*Variegations.*—None.

*Discoloration.*—The general tonality at the end of the first day: JHS 2904 (light greenish yellow). At the end of the third day: JHS 2903 (pale greenish yellow).

*Fragrance.*—Slight, *r. foetida* type.

*Flowering season.*—Typical from the end of May to the end of November.

*Flowering time following planting.*—Variable, depends, for example, on time of year when planted, typical two to eight months after planting.

Petals:

*Texture.*—Smooth on both upper and lower surfaces, thick petals.

*Shape.*—Obovate.

*Margin.*—Round. Apex Shape: Orbicular. Base Shape: Obtuse.

*Size.*—Typical petal width about 1.4 inches; typical petal length about 1.6 inches.

*Form.*—Flat.

*Arrangement.*—Regularly arranged.

*Petaloids.*—Number: 1–2. Color: JHS 2904 (light greenish yellow).

*Persistence.*—Drop off cleanly before drying.

*Lastingness.*—On the plant: Fair (about 2–3 days). As a cut flower: Fair (about 2–3 days).

Reproductive parts:

*Stamens.*—Number: 77. Length: 0.4 inches. Anthers: Length: 0.12 inches. Color: JHS 2203 (light reddish yellow). Arrangement: Tucked in calyx or partly so. Filaments: Color: JHS 2205 (vivid reddish yellow). Length: 0.28 inches. Pollen: Color: JHS 1907 (strong yellow orange), small quantity.

*Pistils.*—Number: 30. Length: 1.4 inches. Styles: Color: JHS 0113 (deep pink). Length: 1.2 inches. Stigmas: Color: JHS 2203 (light reddish yellow). Length: 0.32 inch.

*Hips.*—Color: JHS 1605 (vivid orange). Size: 0.68 inch by 0.6 inch. Shape: Round.

*Seeds.*—Shape: Generally oval with somewhat pointed ends. Size: Typically about 0.24 inch long and about 0.16 inch in diameter. Color: JHS 1903 (light yellowish orange). Quantity: Typically about five seeds per rose hip.

PLANT

*Form.*—Bush.

*Growth.*—Vigorous.

*Age at maturity.*—Three years.

*Mature plant.*—Height: 5.3 feet to 5.6 feet. Width: 4.6 feet.

Foliage: Number of leaflets on normal mid-stem leaves: Seven.

*Size.*—Medium, about 4.8 inches long×3.2 inches wide. Typical leaf petiole length about 0.8 inch. Typical leaf petiole diameter about 0.04 inch.

*Quantity.*—Abundant. Typical leaf quantity per lateral stem — 7.

*Internode length.*—Typical internode length about 1.2 inches to about 1.8 inches.

*Color.*—New foliage: Upper side: JHS 3110 (dull yellow green). Lower side: JHS 3107 (dark yellow green). Old foliage: Upper side: JHS 3508 (dark yellow green). Lower side: JHS 3508 (dark yellow green).

Leaflets:

*Size.*—About 2.2 inches long×1.2 inches wide.

*Shape.*—Elliptic.

*Base shape.*—Rounded.

*Apex shape.*—Acute.

*Upper surface.*—Glossy.

*Lower surface.*—Glossy.

*Edge.*—Serrated.

*Serrations.*—Small.

*Petiole.*—Color: JHS 3507 (deep yellow green). Length: Typical about 0.6 inch. Diameter: About 0.04 inch.

*Petiole rachis.*—Color: JHS 3505 (light yellow green). Underside: Rough.

*Auricle shape, if present.*—None present.

*Stipules.*—Shape: Adnate, generally, straight base and acute apex; serrated. Length: Typical 0.6 inch. Width:

Typical about 0.2 inch. Number: 2 per petiole. Texture: Upper and lower surfaces — rough. Upper Surface Color: JHS 3513 (dull yellow green). Lower Surface Color: JHS 0112 (dull pink).

*Disease resistance.*—Resistant to mildew, rust and black spot under normal growing conditions.

*Pest resistance.*—Resistant.

*Vein color.*—Both upper and lower surfaces. JHS 3304 (light yellow green).

*Venation pattern.*—Reticulate.

Wood:

*New wood.*—Color: JHS 3110 (dull yellow green). Bark: Smooth.

*Old wood.*—Color: JHS 3513 (dull yellow green). Bark: Smooth.

Prickles:

*Quantity.*—On main canes from base: Ordinary; On laterals from main canes: Few; Typical lateral stem has from about ten to fifteen prickles.

*Form.*—Hooked downward.

*Size.*—Length: 0.2 inches; Diameter of prickle base about 0.2 inch.

*Color when young.*—JHS 3103 (light yellowish green).

*Color when mature.*—JHS 1914 (light yellowish green).

Small prickles:

*Quantity.*—On main stalks: None. On laterals: None.

Winter hardiness: Hardy in Japan where grown and observed, not otherwise tested.

I claim:

1. A new and distinct variety of rose plant of the *Rosa* L. class, substantially as herein shown and described, characterized particularly by being bushy, with flat shaped yellow flowers.

* * * * *